United States Patent
Hill et al.

(10) Patent No.: US 8,417,334 B2
(45) Date of Patent: Apr. 9, 2013

(54) METHOD AND APPARATUS FOR ELECTRICALLY STIMULATING THE NERVOUS SYSTEM TO IMPROVE VENTRICULAR DYSFUNCTION, HEART FAILURE, AND OTHER CARDIAC CONDITIONS

(75) Inventors: Michael R. S. Hill, Minneapolis, MN (US); Gary W. King, Fridley, MN (US); Thomas J. Mullen, Ham Lake, MN (US); Xiaohong Zhou, Plymouth, MN (US)

(73) Assignee: Medtronic, Inc., Minneaspolis, MN (US)

( * ) Notice: Subject to any disclaimer, the term of this patent is extended or adjusted under 35 U.S.C. 154(b) by 1940 days.

(21) Appl. No.: 10/039,307

(22) Filed: Oct. 26, 2001

(65) Prior Publication Data
US 2002/0107553 A1 Aug. 8, 2002

Related U.S. Application Data

(60) Provisional application No. 60/294,072, filed on May 29, 2001, provisional application No. 60/243,393, filed on Oct. 26, 2000, provisional application No. 60/243,536, filed on Oct. 26, 2000, provisional application No. 60/243,609, filed on Oct. 26, 2000.

(51) Int. Cl.
*A61N 1/365* (2006.01)
(52) U.S. Cl.
USPC .................................................. 607/9
(58) Field of Classification Search ............... 600/373, 600/374, 377, 381, 382, 384, 509; 607/4–7, 607/9–11, 17, 119, 120, 122
See application file for complete search history.

(56) References Cited

U.S. PATENT DOCUMENTS

| | | | |
|---|---|---|---|
| 3,421,511 A | 1/1969 | Schwartz et al. | |
| 3,522,811 A | 8/1970 | Schwartz, et al. | |
| 3,645,267 A | 2/1972 | Hagfors | |
| 3,650,277 A * | 3/1972 | Sjostrand et al. | 607/44 |
| 3,796,221 A | 3/1974 | Hagfors | |

(Continued)

FOREIGN PATENT DOCUMENTS
FR 2 805 469 A1 * 2/2000

OTHER PUBLICATIONS

Braunwald, M.D. et al., Carotid Sinus Nerve Stimulation in the Treatment of Angina Pectoris and Supraventricular Tachycardia, Mar. 1970, California Medicine, The Western Journal of Medicine, 112 (3): 41-50.

(Continued)

*Primary Examiner* — Christopher D Koharski
*Assistant Examiner* — Frances Oropeza
(74) *Attorney, Agent, or Firm* — Reed A. Duthler; Stephen W. Bauer

(57) ABSTRACT

A method and apparatus are used to provide therapy to a patient experiencing ventricular dysfunction or heart failure. At least one electrode is located in a region associated with nervous tissue, such as nerve bundles T1-T4, in a patient's body. Electrical stimulation is applied to the at least one electrode to improve the cardiac efficiency of the patient's heart. One or more predetermined physiologic parameters of the patient are monitored, and the electrical stimulation is adjusted based on the one or more predetermined physiologic parameters.

11 Claims, 7 Drawing Sheets

U.S. PATENT DOCUMENTS

| | | | |
|---|---|---|---|
| 4,146,029 A | 3/1979 | Ellinwood, Jr. | |
| 4,428,378 A | 1/1984 | Anderson et al. | |
| 4,458,696 A | 7/1984 | Larimore | |
| 4,694,835 A | 9/1987 | Strand | |
| 4,903,701 A | 2/1990 | Moore et al. | |
| 5,031,618 A | 7/1991 | Mullett | |
| 5,058,584 A | 10/1991 | Bourgeois | |
| 5,135,004 A | 8/1992 | Adams et al. | |
| 5,149,713 A | 9/1992 | Bousquet | |
| 5,199,428 A | 4/1993 | Obel et al. | |
| 5,203,326 A * | 4/1993 | Collins | 607/4 |
| 5,213,098 A * | 5/1993 | Bennett et al. | 607/18 |
| 5,220,917 A | 6/1993 | Cammilli et al. | |
| 5,243,980 A | 9/1993 | Mehra | |
| 5,292,336 A | 3/1994 | Spence, Jr. et al. | |
| 5,292,338 A | 3/1994 | Bardy | |
| 5,330,505 A | 7/1994 | Cohen | |
| 5,330,507 A | 7/1994 | Schwartz | |
| 5,330,515 A | 7/1994 | Rutecki et al. | |
| 5,331,996 A | 7/1994 | Ziehm | |
| 5,342,409 A | 8/1994 | Mullett | |
| 5,356,425 A | 10/1994 | Bardy et al. | |
| 5,411,531 A | 5/1995 | Hill et al. | |
| 5,464,434 A | 11/1995 | Alt | |
| 5,496,363 A | 3/1996 | Burgio et al. | |
| 5,564,434 A | 10/1996 | Halperin et al. | |
| 5,607,418 A | 3/1997 | Arzbaecher | |
| 5,700,282 A | 12/1997 | Zabara | |
| 5,792,187 A | 8/1998 | Adams | |
| 5,817,131 A | 10/1998 | Elsberry et al. | |
| 5,824,021 A | 10/1998 | Rise | |
| 6,006,134 A | 12/1999 | Hill et al. | |
| 6,058,328 A * | 5/2000 | Levine et al. | 607/14 |
| 6,058,331 A | 5/2000 | King | |
| 6,073,048 A | 6/2000 | Kieval et al. | |
| 6,134,470 A | 10/2000 | Hartlaub | |
| 6,178,349 B1 | 1/2001 | Kieval | |
| 6,272,377 B1 * | 8/2001 | Sweeney et al. | 600/515 |
| 6,400,982 B2 * | 6/2002 | Sweeney et al. | 600/515 |
| 6,937,898 B2 * | 8/2005 | Limousin | 607/14 |
| 2002/0004549 A1 | 1/2002 | Custodero et al. | |
| 2002/0107553 A1 | 8/2002 | Hill et al. | |
| 2002/0143369 A1 | 10/2002 | Hill et al. | |
| 2002/0165586 A1 | 11/2002 | Hill et al. | |
| 2003/0100924 A1 | 5/2003 | Foreman et al. | |
| 2003/0212445 A1 | 11/2003 | Weinberg | |

OTHER PUBLICATIONS

Bilgutay, M.D., et al., Vagal Tuning—A New Concept in the Treatment of Supraventricular Arrhythmias, Angina Pectoris, and Heart Failure, Jul. 1968, Journal of Thorac Cardiovascular Surgery 56 (1): 71-82.
Foreman, et al., Modulation of Intrinsic Cardiac Neurons by Spinal Cord Stimulation: Implications for its Therapeutic Use in Angina Pectoris, Apr. 10, 2000, Cardiovascular Research, pp. 367-375.
Bilgutay, et al., "Vagal Tuning," from *Journal of Thoracic & Cardiovascular Surgery*, Jul. 1968, 56:71-82.
Braunwald, et al., "Carotid Sinus Nerve Stimulation in the Treatment of Angina Pectoris and Supraventricular Tachycardia," from *California Medicine, The Western Journal of Medicine*, Mar. 1970, 112(3):41-50.
Armour, "Instant-to-Instant Reflex Cardiac Regulation," 1976, 309-328.
Schwartz, et al., "Effect of dorsal root section on the arrhythmias associated with coronary occlusion," from *American Journal of Physiology*, Sep. 1976, pp. 923-928.
Blair, et al., "Responses of Thoracic Spinothalamic Neurons to Intracardiac Injection of Bradykinin in the Monkey," from *Circulation Research* vol. 51. No. 1, Jul. 1982, pp. 83-94.
Ammons, et al., "Vagal Afferent Inhibition of Spinothalamic Cell Responses to Sympathetic Afferents and Bradykinin in the Monkey," from *Circulation Research* vol. 53. No. 5, Nov. 1983, pp. 603-612.
Blair, et al., "Responses of Thoracic Spinothalamic and Spinoreticular Cells to Coronary Artery Occlusion," from *Journal of Neurophysiology* vol. 51. No. 4, Apr. 1984, pp. 636-648.
Ammons, et al., "Effects of intracardiac bradykinin on $T_2$—$T_3$ medial spinothalamic cells," from *American Journal of Physiology*, 1985, pp. R147-R152.
Blair, et al., "Activation of Feline Spinal Neurons by Potentiated Ventricular Contractions and Other Mechanical Cardiac Stimuli," from *Journal of Physiology*, 1988, pp. 649-667.
Schwartz, et al., "Autonomic Mechanisms And Sudden Death—New Insights From Analysis of Baroreceptor Reflexes in Conscious Dogs With and Without a Myocardial Infarction," from *Circulation*, vol. 78, No. 4, Oct. 1988, pp. 970-979.
Hobbs, et al., "Cardiac and Abdominal Vagal Afferent Inhibition of Primate $T_9$—$S_1$ Spinothalamic Cells," from *The American Physiological Society*, 1989, pp. R889-R895.
Butler, et al., "Cardiac Responses to Electrical Stimulation of Discrete Loci in Canine Atrial and Ventricular Ganglionated Plexi," from *The American Physiological Society*, 1990, pp. H1365-H1373.
Hull, et al., "Heart Rate Variability Before and After Myocardial Infarction in Conscious Dogs At High and Low Risk of Sudden Death," from *The American College of Cardiology*, 1990, pp. 978-985.
Armour, M.D., "Intrinsic Cardiac Neurons," from *Journal of Cardiovascular Electrophysiology*, vol. 2, No. 4, Aug. 1991, pp. 331-341.
Chandler, et al., "Effects of Vagal Afferent Stimulation on Cervical Spinothalamic Tract Neurons in Monkeys," from *Pain*, 1991, pp. 81-87.
Linderoth, M.D., et al., "Effects of Sympathectomy on Skin and Muscle Microcirculation During Dorsal Column Stimulation: Animal Studies," from *Neurosurgery*, vol. 29, No. 6, 1991, pp. 874-879.
Vanoli, et al., "Vagal Stimulation and Prevention of Sudden Death in Conscious Dogs With a Healed Myocardial Infarction," from *Circulation Research*, vol. 68, No. 5, May 1991, pp. 1471-1481.
Cardinal, et al., "Distinct Activation Patterns of Idiovenricular Rhythms and Sympathetically-Induced Ventricular Tachycardias in Dogs With Atrioventricular Block," from *PACE*, Sep. 1992, pp. 1300-1306.
Fu, et al., "Vagal Afferent Fibers Excite Upper Cervical Neurons and Inhibit Activity of Lumbar Spinal Cord Neurons in the Rat," from *Pain*, 1992, pp. 91-100.
Hobbs, et al., "Evidence That $C_1$ and $C_2$ Propriospinal Neurons Meditate the Inhibitory Effects of Viscerosomatic Spinal Afferent Input on Primate Spinothalamic Tract Neurons," from *Journal of Neurophysiology*, vol. 67, No. 4, Apr. 1992, pp. 852-860.
Hobbs, et al., "Segmental Organization of Visceral and Somatic Input Onto $C_3$—$T_6$ Spinothalamic Tract Cells of the Monkey," from *Journal of Neurophysiology*, vol. 68, No. 5, Nov. 1992, pp. 1575-1588.
Chandler, et al., "A Mechanism of Cardiac Pain Suppression by Spinal Cord Stimulation: Implications for Patients With Angina Pectoris," from *European Heart Journal*, 1993, pp. 96-105.
Huang, et al., "Effects of Transient Coronary Artery Occlusion on Canine Intrinsic Cardiac Neuronal Activity," from *Integrative Physiological and Behavioral Science*, vol. 28, No. 1, Jan.-Mar. 1993, pp. 5-21.
Adamson, et al., "Unexpected Interaction Between β-Adrenergic Blockage and Heart Rate Variability Before and After Myocardial Infarction—A Longitudinal Study in Dogs At High and Low Risk for Sudden Death," from *American Heart Association, Inc.*, 1994, pp. 976-382.
Ardell, "Structure and Function of Mammalian Intrinsic Cardiac Neurons," from *Neurocardiology*, 1994, pp. 95-114.
Armour, "Peripheral Autonomic Neuronal Interactions in Cardiac Regulation," from *Neurocardiology*, 1994, pp. 219-244.
Foreman, "Spinal Cord Neuronal Regulation of the Cardiovascular System," from *Neurocardiology*, 1994, pp. 245-276.
Hull, et al., "Exercise Training Confers Anticipatory Protection From Sudden Death During Acute Myocardial Ischemia," from *Circulation*, 1994, pp. 548-552.
Linderoth, et al., "Sympathetic Mediation of Peripheral Vasodilation Induced by Spinal Cord Stimulation: Animal Studies of the Role of Cholinergic and Adrenegic Receptor Subtypes," from *Neurosurgery*, vol. 35, No. 4, Oct. 1994, pp. 711-719.
Yuan, et al., "Gross and Microscopic Anatomy of the Canine Intrinsic Cardiac Nervous System," from *The Anatomical Record*, 1994, pp. 75-87.

Chandler, et al., "Vagal, Sympathetic and Somatic Sensory Inputs to Upper Cervical ($C_1$—$C_3$) Spinothalamic Tract Neurons in Monkeys," from *The American Physiological Society*, 1996, pp. 2555-2567.

Zhang, et al., "Thoracic Visceral Inputs Use Upper Cervical Segments to Inhibit Lumbar Spinal Neurons in Rats," from *Brain Research*, 1996, pp. 337-342.

Armour, et al., "Gross and Microscopic Anatomy of the Human Intrinsic Cardiac Nervous System," from *The Anatomical Record*, 1997, pp. 289-298.

Croom, et al., "Cutaneous Vasodilation During Dorsal Column Stimulation Is Mediated by Dorsal Roots and CGRP," from *The American Physiological Society*, 1997, pp. H950-H957.

Hautvast, et al., "Spinal Cord Stimulation in Chronic Intractable Angina Pectoris: A Randomized, Controlled Efficacy Study," from *American Heart Journal*, vol. 136, No. 6, 1998, pp. 1114-1120.

Schwartz, et al., "Autonomic Mechanisms and Sudden Death—New Insights From Analysis of Baroreceptor Reflexes in Conscious Dogs With and Without Myocardial Infarction," from *Circulation*, vol. 78, No. 4, Oct. 1988, pp. 969-979.

Barron, et al., "Spinal Integration of Antidromic Mediated Cutaneous Vasodilation During Dorsal Spinal Cord Stimulation in the Rat," from *Neuroscience Letter*, 1999, pp. 173-176.

Foreman, "Mechanisms of Cardiac Pain," from *Annu. Rev. Physiol.*, 1999, pp. 143-167.

Linderoth, et al., "Physiology of Spinal Cord Stimulation: Review and Update," from *Neuromodulation*, vol. 2, No. 3, 1999, pp. 150-164.

Qin, et al., "Chemical Activation of Cervical Cell Bodies: Effects on Responses to Colorectal Distension in Lumbosacral Spinal Cord of Rats," from *The American Physiological Society*, 1999, pp. 3423-3433.

Chandler, et al., "Intrapericardiac Injections of Algogenic Chemicals Excite Primate $C_1$—$C_2$ Spinothalamic Tract Neurons," from *The American Physiological Society*, 2000, pp. R560-R568.

Foreman, et al., "Modulation of Intrinsic Cardiac Neurons by Spinal Cord Stimulation: Implications for Its Therapeutic Use in Angina Pectoris," from *Cardiovascular Research*, 2000, pp. 367-375.

Hopkins, et al., "Pathology of Intrinsic Cardiac Neurons From Ischemic Human Hearts," from *The Anatomical Record*, 2000, pp. 424-436.

Kember, et al., "Aperodic Stochastic Resonance in a Hysteretic Population of Cardiac Neurons," from *The American Physical Society*, 2000, pp. 1816-1824.

Meyerson, et al., "Spinal Cord Stimulation," from *Bonica's Management of Pain*, 2001, pp. 1857-1876.

Ardell, "Neurohumoral Control of Cardiac Function," from *Heart Physiology and Pathophysiology*, Fourth Edition, 2001, pp. 45-59.

Farrell, et al., "Angiotensin II Modulates Catecholamine Release Into Interstitial Fluid of Canine Myocardium In Vivo," from *Am J. Physiol. Heart Cir. Physiol.*, 2001, pp. H813-H822.

Kingma, Jr., et al., "Neuromodulation Therapy Does Not Influence Blood Flow Distribution or Left-Ventricular Dynamics During Acute Myocardial Ischemia," from *Autonomic Neuroscience: Basic & Clinical*, 2001, pp. 47-54.

Tanaka, et al., "Low Intensity Spinal Cord Stimulation May Induce Cutaneous Vasodilation Via CGRP Release," from *Brain Research*, 2001, pp. 183-187.

Qin, et al., "Responses and Afferent Pathways of Superficial and Deeper $C_1$—$C_2$ Spinal Cells to Intrapericardial Algogenic Chemicals in Rats," from *The American Physiological Society*, Dec. 2000, pp. 1522-1532.

Armour, et al., "Long-Term Modulation of the Intrinsic Cardiac Nervous System by Spinal Cord Neurons in Normal and Ischaemic Hearts," from *Autonomic Neuroscience: Basic & Clinical*, 2002, pp. 71-79.

Chandler, et al., "Spinal Inhibitory Effects of Cardiopulmonary Afferent Inputs in Monkeys: Neuronal Processing in High Cervical Segments," from *J. Neurophysical*, 2002, pp. 1290-1302.

Cardinal, et al., "Spinal Cord Activation Differentially Modulates Ischaemic Electrical Responses to Different Stressors in Canine Ventricles," from *Autonomic Neuroscience: Basic & Clinical*, 2004, pp. 37-47.

Ardell, "Intrathoracic Neuronal Regulation of Cardiac Function," from *Basic and Clinical Neurocardiology*, 2004, pp. 118-152.

\* cited by examiner

METHOD AND APPARATUS FOR ELECTRICALLY STIMULATING THE NERVOUS SYSTEM TO IMPROVE VENTRICULAR DYSFUNCTION, HEART FAILURE, AND OTHER CARDIAC CONDITIONS

RELATED CASES

This case claims priority to the following provisionally-filed cases:

U.S. Provisional Patent Application Serial No. 60/294,072, filed May 29, 2001, entitled "Closed-Loop Neuromodulation for Prevention and Treatment of Cardiac Conditions";

U.S. Provisional Patent Application Serial No. 60/243,393, filed Oct. 26, 2000, entitled "Method and Apparatus to Minimize the Effects of a Cardiac Insult";

U.S. Provisional Patent Application Serial No. 60/243,536, filed Oct. 26, 2000, entitled "Method and Apparatus to Minimize the Effects of a Cardiac Insult"; and U.S. Provisional Patent Application Serial No. 60/243,609, filed Oct. 26, 2000, entitled "Method and Apparatus for Electrically Simulating the Nervous System to Improve Ventricular Dysfunction, Heart Failure, and Other Cardiac Conditions", all of which are incorporated herein by reference in their entireties.

This case is related to, and contains subject matter in common with the following applications:

U.S. patent application Ser. No. 09/999,722 filed on Oct. 26, 2001 entitled "Method and Apparatus to Minimize the Effects of a Cardiac Insult", and published as US 2003/0004549.

U.S. patent application Ser. No. 09/999,723 filed on Oct. 26, 2001 entitled "Method and Apparatus to Minimize the Effects of a Cardiac Insult", now U.S. Pat. No. 7,010,345.

U.S. patent application Ser. No. 10/035,319 filed on Oct. 26, 2001 entitled "Closed-Loop Neuromodulation for Prevention and Treatment of Cardiac Conditions", and published as US 2002/0165586, now issued as U.S. Pat. No. 7,218,964.

FIELD OF THE INVENTION

This invention relates to a method and apparatus for electrically stimulating certain nervous tissue to alter conditions within the heart, and, more particularly, to stimulate nerves to treat ventricular dysfunction or heart failure.

DESCRIPTION OF THE RELATED ART

Various cardiac conditions, such as supraventricular arrhythmias, angina pectoris, and ventricular dysfunction or heart failure, have been treated by electrical stimulation of the spinal cord, vagus and other nerves. Typically, electrodes are implanted in the patient adjacent the spinal area and electrically excited to produce desirable effects on the functioning of the heart. For example, a paper entitled "Vagal Tuning" by Bilgutay et. al., published in the Journal of Thoracic and Cardiovascular Surgery, Vol. 56, No. 1, July 1968, pp. 71-82, discusses a system that delivers electrical stimulation to the vagus nerve using silastic coated, bipolar electrodes, such as those described in U.S. Pat. No. 3,421,511. The electrodes are surgically implanted around the intact nerve or nerves and a controlled current is delivered thereto. The electrodes pass the current to the nerve(s), producing a decreased heart rate while still preserving sinus rhythm in the patient. Low amplitude stimulation has also been employed to control induced tachycardias and ectopic beats.

Angina pectoris and paroxysmal atrio-ventricular junctional or supraventricular tachycardias have also been treated by stimulating the carotid sinus nerve via implanted electrodes. For example, a paper entitled "Carotid Sinus Nerve Stimulation in the Treatment of Angina Pectoris and Supraventricular Tachycardia," published in California Medicine, 112:41-50, March 1970, describes a system in which patients may electrically stimulate their carotid sinus nerve when they sense angina and/or supraventricular tachycardia.

Delivery of electrical stimulation to the nervous system using an implanted electrode has been found particularly effective in the relief of chest pain, such as angina pectoris, that often accompanies myocardial ischemia. For example, U.S. Pat. No. 5,058,584 to Bourgeois, incorporated herein by reference in its entirety, discloses a system and method for treating such chest pain using electrical stimulation within the epidural space of the spinal cord. This treatment is provided only after a symptomatic level of activity is reached as sensed by an accelerometer or other activity sensor. Similarly, U.S. Pat. No. 6,058,331 to King, also incorporated herein by reference in its entirety, discusses a system and method for treating ischemia by automatically adjusting electrical stimulation to the spinal cord, peripheral nerve, or neural tissue ganglia based on a sensed patient condition. U.S. Pat. No. 5,199,428 to Obel et al., incorporated herein by reference in its entirety, discloses a system for stimulating the epidural space with continuous and/or phasic electrical pulses using an implanted pulse generator upon the detection of myocardial ischemia to decrease cardiac workload, and thereby reduce cell death related to the ischemic event. U.S. Pat. No. 5,824,021 to Rise, incorporated herein by reference in its entirety, discusses a system and method for providing spinal cord stimulation to relieve angina, and to further provide a patient notification that an ischemic event is occurring. This spinal cord stimulation is provided only after the ischemia is already detected.

In addition to the above-described systems, other systems have been disclosed to provide nerve stimulation following the onset of predetermined condition. U.S. Pat. No. 6,134,470 to Hartlaub describes a system for utilizing spinal cord stimulation to terminate tachyarrhythmias. The stimulation is provided only after the tachyarrhythmias, or a precursor thereto, has been detected. U.S. Pat. No. 3,650,277 discloses a system for stimulating the left and right carotid sinus nerves in response to the detection of elevated mean arterial blood pressure to alleviate hypertension.

Although it is known that ischema and certain arrhythmias may be treated using electrical stimulation of the nervous system via implanted electrodes, it has not heretofore been known to utilize electrical stimulation of nerves or other body tissue to treat ventricular dysfunction, heart failure, or imbalance of autonomic tone or neuro-endocrinological system in a manner that improves cardiac performance and efficiency of the heart.

Typically, patients with ventricular dysfunction or heart failure have a reduced capacity for myocardial function. The heart is unable to adequately meet the metabolic demands of the body by providing the appropriate blood flow. This may result in increased blood pressure (afterload), and increased volume retention (preload). Thus, common symptoms of ventricular dysfunction or heart failure include fatigue, which is caused by the low cardiac output, and edema and swelling, which is caused by fluid overload.

Ventricular dysfunction or heart failure is predominantly the result of an imbalance in the neuro-endocrinological systems, including the sympathetic and the renin-angiotensin systems. Prior methods of treatment include the administration of drugs that interfere with the cyclical nature of the neuro-endocrine feedback. For example, ACE inhibitors may be prescribed to decrease the effects of angiotensin I and II, and to reduce the afterload and preload. Beta-blockers have also been shown to reduce afterload, and may further decrease contractility. This provides greater relaxation for the heart myocardium.

Treating ventricular dysfunction or heart failure through the prescription of drugs, however, is problematic. The dosages are patient dependant, and thus titration of the drug amounts must be performed on a patient-by-patient basis. Generally, this involves invasive or non-invasive follow-up procedures, and a reassessment of the treatment. This type of trial-and-error process may be lengthy and frustrating. Additionally, many patients experience unpleasant side-effects from some ventricular dysfunction or heart failure medications. For example, some asthmatics cannot take beta-blockers because of global side effects due to contra-indications. Moreover, effective treatment in this situation depends on patient compliance with the prescribed treatment dosages and schedules. However, not all patients comply with the recommendations of their physician. What is needed, therefore, is an alternative treatment that may be used to replace, or to augment, the administration of drugs in treating ventricular dysfunction or heart failure or imbalance of autonomic tone.

SUMMARY OF THE INVENTION

In one aspect of the instant invention, a method is provided for treating ventricular dysfunction, heart failure, or imbalance of autonomic tone or neuro-endocrinological system. At least one electrode is provided in a region associated with nervous tissue in a patient's body. Electrical stimulation is provided via the at least one electrode to improve the cardiac performance (e.g. hemodynamics) and efficiency (e.g. balance between supply and demand) of the patient's heart.

In another aspect of the instant invention, an apparatus is provided for treating ventricular dysfunction, heart failure, or imbalance of autonomic tone. At least one electrode is located in a region associated with nervous tissue in a patient's body. Means are included for applying electrical stimulation via the at least one electrode to improve the cardiac performance and efficiency of the patient's heart.

In still another aspect of the instant invention, a method is provided. The method comprises providing at least one electrode in a region associated with nervous tissue in a patient's body. Electrical stimulation is applied via the at least one electrode to alter the functioning of a patient's heart. One or more predetermined physiologic parameters of the patient are monitored, and the electrical stimulation is adjusted based on the one or more predetermined physiologic parameters.

In another embodiment, an apparatus is provided comprising at least one electrode that may be positioned in a region associated with nervous tissue in a patient's body. Means for controlling the delivery of stimulation to alter functioning of a patient's heart is also provided. The controlling means is capable of utilizing one or more predetermined physiologic parameters of the patient, and the electrical stimulation is adjusted based on the one or more predetermined physiologic parameters.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of a method and apparatus for providing improved cardiac function according to the present invention are shown in the Figures. As will be readily apparent to those skilled in the art upon a complete reading of the present application, the present method and apparatus are applicable to a variety of systems other than the embodiment illustrated herein.

Figure 1A:
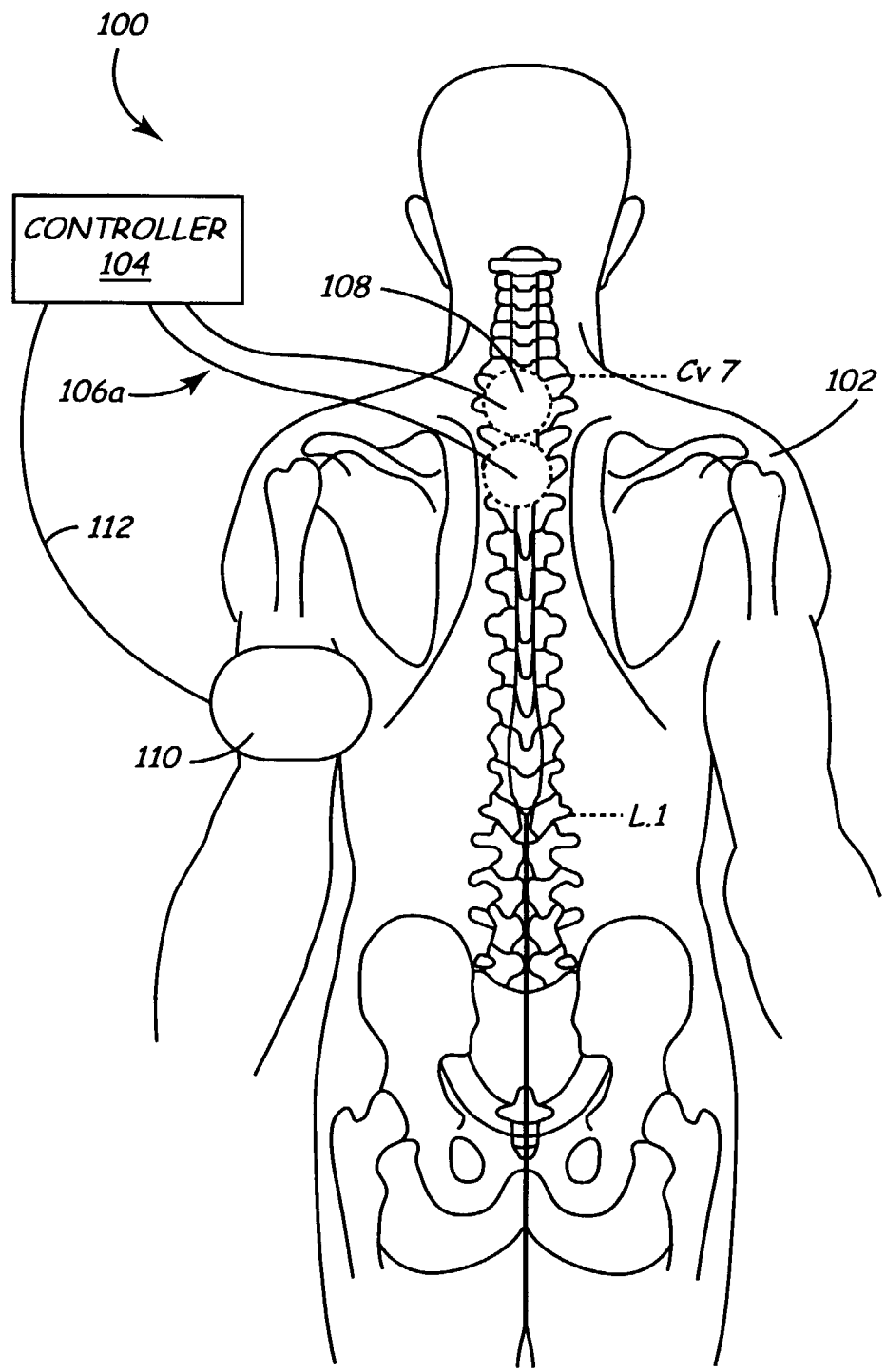
FIG. 1A illustrates a stylized representation of a posterior view of a patient with electrodes positioned thereon.
Figure 1B:
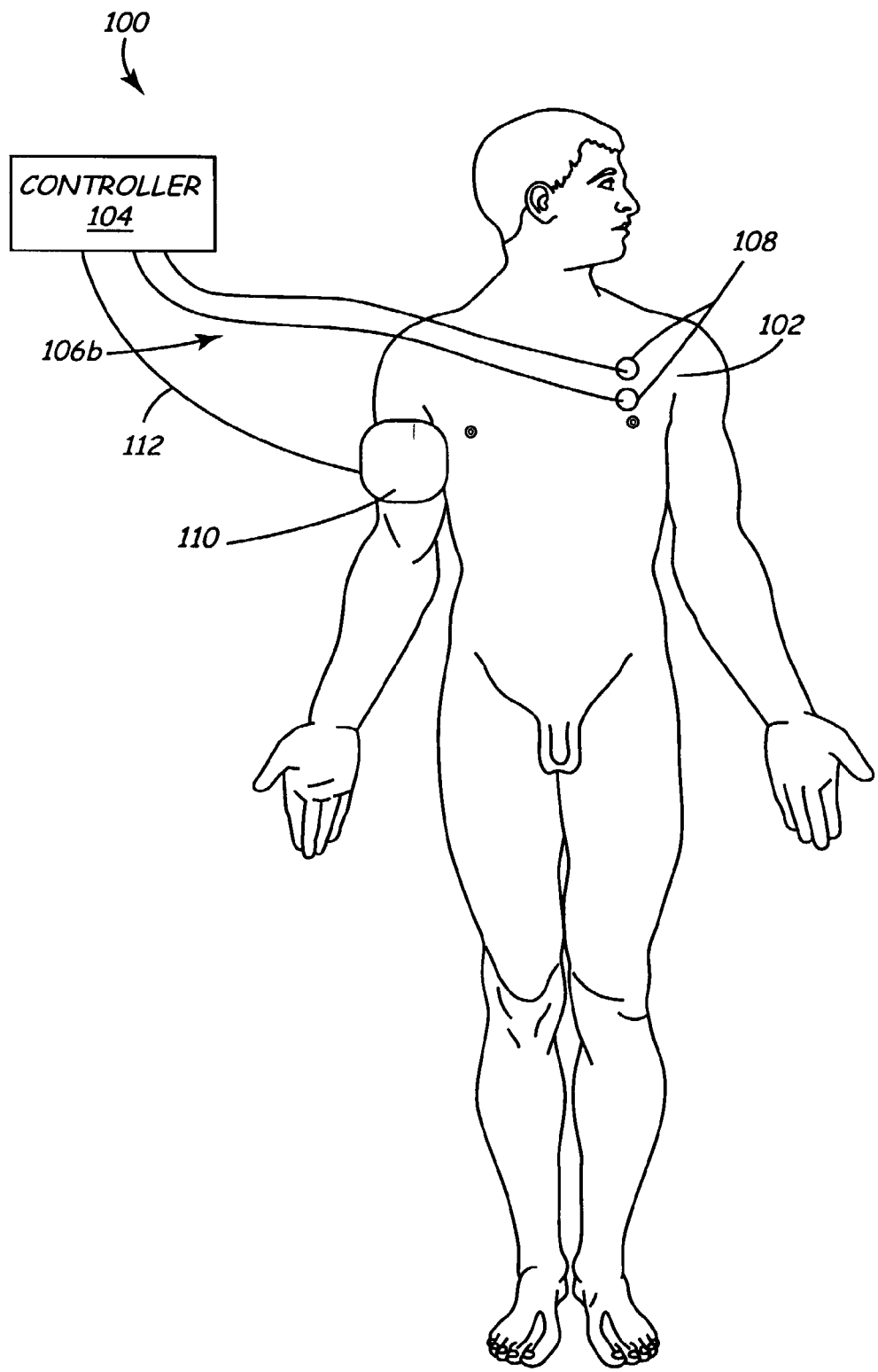
FIG. 1B illustrates a stylized representation of an anterior view of a patient with electrodes positioned thereon.

Generally, the instant invention is directed to a method and apparatus for improving cardiac performance (e.g., hemodynamics) and efficiency (e.g., balance between supply and demand and balance within the neuro-endocrinological systems) of the patient's heart. In the illustrated embodiment, the current invention utilizes electrical stimulation to treat ventricular dysfunction or heart failure. As shown in FIGS. 1A and 1B, a system 100 may provide stimulation (e.g. SCS, TENs, sub-cutaneous) to a patient 102 adjacent one or more of the locations T1-T12, and C1-C8 or to nerves on the chest, to improve cardiac performance and efficiency. Such stimulation has been shown to improve cardiac contractility, to further improve the pressure-volume relationship within the heart, to reduce sympathetic activity of the cardiac tissue, to improve the cardiac condition, and to reduce the likelihood of ventricular arrhythmias. Thus, the electrical stimulation produces effects similar to those induced by prescription beta-adrenergic receptor blocking drugs. SCS has been shown to vasodilate peripheral arterioles and increase blood flow to the limbs. SCS may further cause the production of neuropeptides such as CGRP, NO, and VIP that are known vasodilators, which may assist in redirection of blood flow from regions of high flow to regions of low flow. This further improves the performance and efficiency of the heart. In the ischemic dilated cardiomyopathy patients, this therapy may suppress or reduce sub-endocardial ischemia, and hence be cardioprotective. Electrical stimulation may further result in improvements in operational efficiency and function of cardiac tissue even in the presence of reduced blood supply.

A controller 104 is coupled through conventional conductive links 106, such as leads or wires, to one or more electrodes 108 mounted in a region adjacent the T1-T12 and C1-C8 vertebrae and their associated nerve bundles. The electrodes 108 may take on any of a variety of forms, including but not limited to conventional surface mounted electrodes, such as are commonly used in conjunction with Transcuteous Neurological Stimulators (TENS) units. These surface mounted electrodes may be fixed to the patient 102 via any of a variety of conventional mechanical or chemical mechanisms or may be simply held in place by friction and gravity. Alternatively, conventional implantable electrodes may be surgically inserted into the spinal region adjacent the T1-T12 and C1-C8 vertebrae, and may be located near or even immediately adjacent the T1-T12 and C1-C8 nerve bundles for spinal cord stimulation.

Implantable electrodes may be placed subcutaneously to stimulate underlying muscles, overlying cutaneous nerves, or passing somatic nerves. For example, lead Model 3987, On Point®, is a peripheral nerve stimulation lead available from Medtronic, Inc. with four contacts and a polyester mesh skirt for fixation to subcutaneous tissue or muscle fascia. Other Medtronic leads might also be used, including Model 3587A or Model 3998, which have an insulative paddle enlargement, or Model 3487A or Model 3888, which do not. In both surface mounted and implanted electrodes, electrical signals supplied by the controller 104 to the electrodes 108 electrically stimulate nervous tissue in the spinal canal.

Implantable electrodes may be placed adjacent to nerves such as the median, peroneal, ulnar, and ansalenticularis nerves to provide stimulation according to the current invention. Similarly, implantable electrodes may be placed near the vagus nerves, carotid sinus, and all other cranial nerves to provide stimulation. Finally, implantable electrodes may be placed epicardially or transvenously near the cardiac ganglia or plexi and also employed in this manner.

The controller 104 may take the form of an external device or an implantable device. Where the controller 104 is an external device, it may be useful in providing therapeutic signals to a patient who is experiencing an unexpected cardiac event, such as a first or otherwise unanticipated episode of ventricular dysfunction, heart failure, cardiovascular collapse, etc. However, where the patient has a history of cardiac events, it may prove useful to construct the controller 104 in a housing designed to be implantable within the human body, such as is common in cardiac pacemakers and defibrillators. The controller 104 may be programmed for either automatic or manual operation. That is, the controller 104 may have one or more conventional sensors (not shown) of a type capable of sensing a cardiac event or a precursor to a cardiac event in the patient, e.g., a decompensation episode of ventricular dysfunction, heart failure, and cardiovascular collapse. The sensors and control scheme used to detect the cardiac event or a precursor to a cardiac event may be conventional, such as is found in implantable defibrillators or pacemakers. Upon detection of the cardiac event, the controller 104 may automatically begin therapeutic treatment of the patient by electrically stimulating the T1-T12 nerve bundles. Alternatively, a patient or authorized person may manually activate the controller 104 to begin this therapeutic treatment. Manual activation may be accomplished by any of a variety of mechanisms. For example, where the controller 104 is implanted in the patient, activation may be accomplished by wireless communication or the like.

Figure 1C:
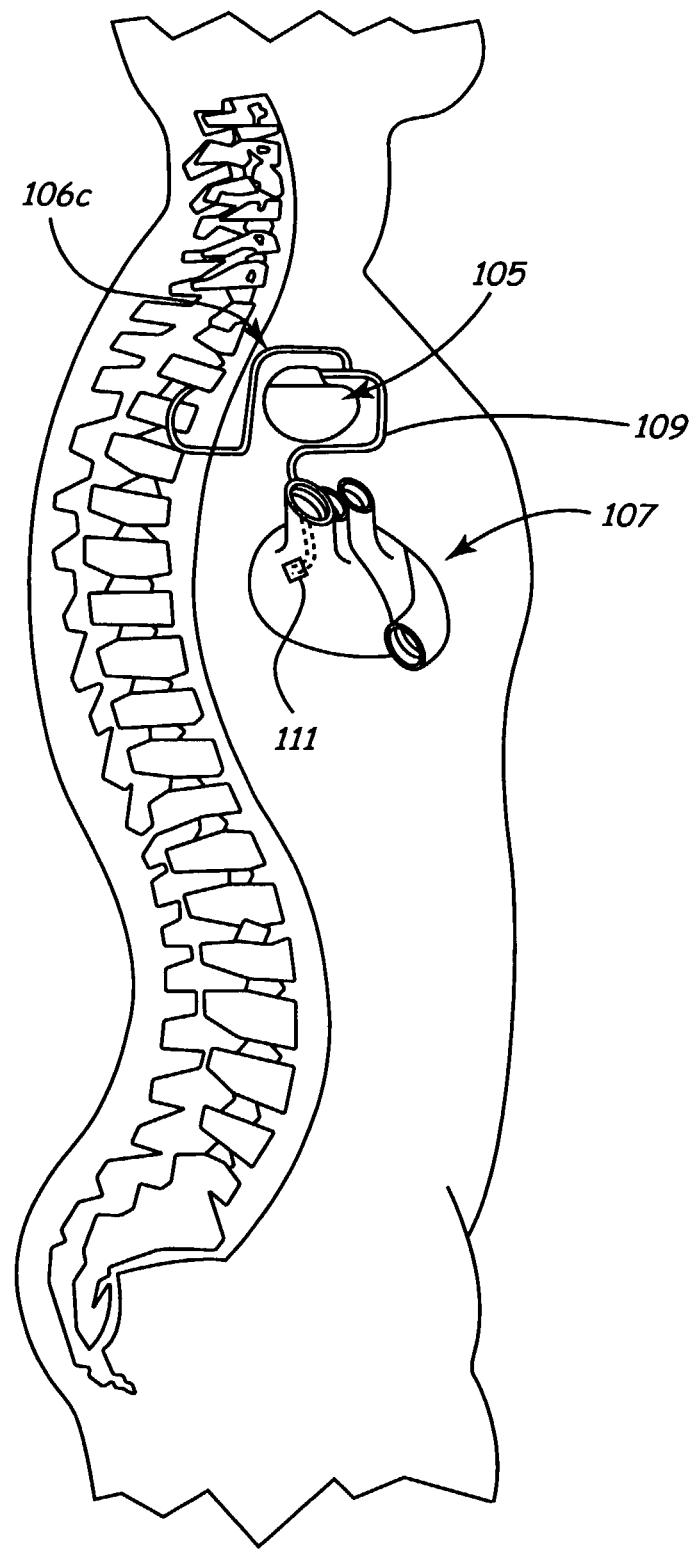
FIG. 1C is a diagram illustrating an implantable stimulation device implanted within a patient.

In those situations in which a patient has a history of cardiac events, it is generally useful to construct the controller 104 in a housing 105 designed to be implantable within the human body, as shown in FIG. 1C. In this embodiment, implanted lead 106c is employed to deliver SCS according to the invention. This housing may optionally include a pacing and/or cardioverter/defibrillator stimulation circuit for generating cardiac stimulation signals to the heart 107 using one or more leads 109, as is known in the art. Leads 109 may carry one or more physiological sensors 111 for sensing physiological signals, as is discussed below. Additionally, or in the alternative, the housing may also include a drug delivery device such as a drug pump coupled to a drug delivery catheter that may be used with the nerve stimulation to provide a biologically-active agent to tissue to prevent anticipated or detected physiological insults.

The therapeutic treatment administered by the controller 104 may take on a variety of different forms. In one embodiment, SCS may be used to titrate the pressure-volume relationship of the heart in conjunction with other types of therapy, such as one or more types of pacing therapies. For example, an adjustment of the Atrial-to-Ventricular and Ventricular-Ventricular timing during atrial-synchronized bi-ventricular pacing (cardiac resynchronization therapy) may be performed at about the same time as the SCS to further improve the performance and efficiency of the heart.

Additionally, the stimulation therapy may be administered along with cardiac resynchronization therapy to further improve the cardiac performance and efficiency of the heart. That is, the SCS or another stimulation (e.g. TENs, subcutaneous) therapy may be administer shortly before, shortly after, or at the same time as resynchronization or other pacing therapy. For example, the SCS therapy may be administered in conjunction with bradycardia pacing therapy, such as changes in the lower rate limit (LRL—atrial or ventricle); therapies for increasing cardiac output or pulse pressure, such as post extra-systolic potentiation (PESP) pacing or non-excitatory stimulation (NES) pacing; and/or therapies for preventing arrhythmias or reducing arrhythmic burden, such including arrhythmia prevention pacing algorithms, such as consistent A or V pacing and rate stabilization pacing. In particular, one exemplary scheme involves administering the stimulation therapy in conjunction with overdrive RV apical pacing to provide improved cardiac output for example in patients with obstructive cardiomyopathies. In addition, the therapy may be administered in conjunction with other device therapies to further improve the cardiac performance and efficiency of the heart. These device therapies may include, but are not limited to, drug delivery device therapies, automatic external defibrillation therapies, treatments provided by monitoring or diagnostic devices, and therapies provided in conjunction with patient management and information tools.

In one embodiment, delivery of the SCS therapy may be modified based on a variety of measurable physiologic parameters. As depicted in FIGS. 1A and 1C, representative sensors 110 and/or 111 may be positioned adjacent or within the body of the patient 102 to sense various physiological conditions, which are communicated back to the controller 104 over leads 112. The measured physiological conditions may be used as an indication of the patient's response to the therapy being administered by the controller 104. That is, a positive physiological response may be used as an indication that the therapy is achieving the desired result. The sensed physiological conditions may be used to adjust the parameters of the SCS. For example, the controller 104 may measure and record cardiac pressure. A change in the cardiac pulse pressure may be used in a closed-loop system to adjust delivery of SCS. For example, if the controller 104 detects that the cardiac pulse pressure has declined over time, then the parameters of the SCS may be adjusted in an attempt to increase the cardiac pulse pressure. On the other hand, where the controller 104 observes a consistent, appropriate cardiac pulse pressure, then the stimulation delivered to the T1-T12 nerve bundles may be continued, as a desired result is being achieved by the SCS. On the other hand, where the controller 104 observes continued high, or even rising, cardiac pulse pressure, then the parameters of the SCS may be adjusted in an attempt to lower the cardiac pulse pressure over time.

Other parameters that may be measured and used as feedback in a closed loop control system for the SCS include, but are not limited to, pressure-volume (PV) loops, pressure-area (PA) loops, pressure-dimension (PD) loops, diastolic and systolic pressures, estimated pulmonary artery pressure, change in cardiac pulse pressure, pre-ejection timing intervals, heart rate measures (such as, rates, intervals, and the like), autonomic indicators (such as, heart rate variability, direct neural recordings, and the like), chemical sensors (such as, catecholamines, O2, pH, CO2, and the like), or non-cardiac physiologic sensors (such as, activity, respiratory rate, time of day, and the like). Those skilled in the art will appreciate that any of a wide variety of measurable physiologic parameters may be monitored and used to implement the closed-loop adaptive controller described herein. An exemplary controller is described in greater detail in co-pending U.S. application No. 10/035,319, entitled "Closed-Loop Neuromodulation for Prevention and Treatment of Cardiac Conditions" filed on even date herewith, and which is hereby incorporated by reference in its entirety.

Any combination of the foregoing may be used to determine the timing, waveforms, and amplitude of the electrical stimulation delivered to the electrodes 108. Those skilled in the art will appreciate that the illustrated, representative sensor 110 may take on any of a variety of forms, depending upon the physiological parameter being sensed. Generally, these feedback parameters may be detected and used to control certain parameters of the stimulation, such as the magnitude, duration, duty cycle, and frequency. Typically, the stimulation falls within the range of about 200-400 microsecond duration pulses, at a frequency in the range of about 50-100 Hz, and at a voltage of up to about 6V. For example, with greater stimulation parameters (increased magnitude, increased frequency, increased duty cycle, and/or increased pulse durations, there is a potential for greater beta-blocker type (withdrawal of sympathetic activity) effect. This would result in decreased contractility, alteration in blood flow (increase in coronary supply), improved cardioprotection and decreased workload or demand. An additional example is the appropriate use of pre-set parameters in response to sensed cardiac event information of the patient. For example, if the patient is having a decompensation ventricular dysfunction or heart failure event, then "more strenuous" stimulation parameters (e.g. increased magnitude, increased pulse width and increased frequency) may be used to provide the greatest amount of protection and local withdrawal of sympathetic activity. For a less severe event, such as an elevation in end diastolic pressure, then "less strenuous" stimulation parameters may be used to provide an incremental adjustment to the cardiac function.

Figure 2:
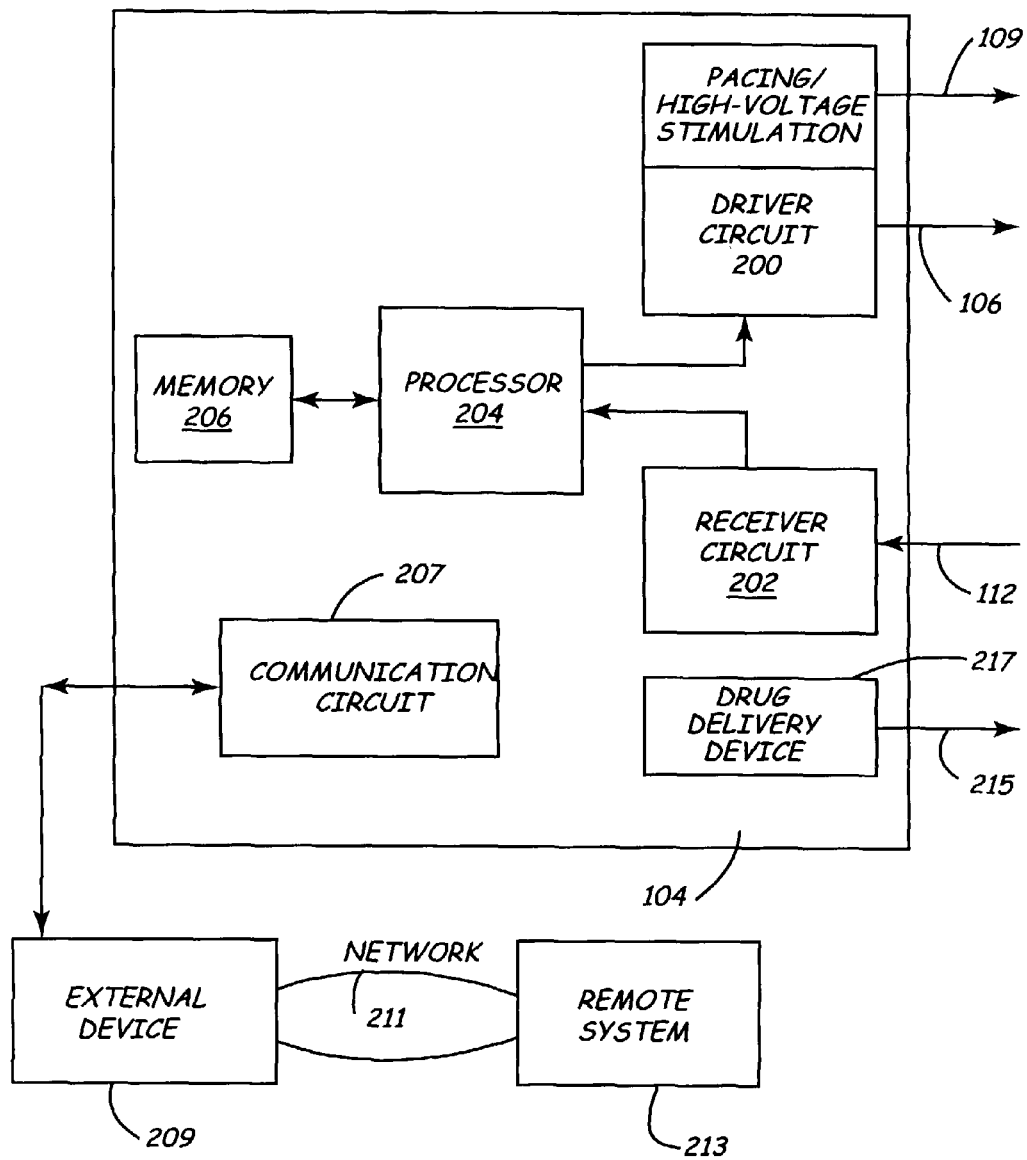
FIG. 2 illustrates a stylized block diagram of a controller of FIG. 1.

FIG. 2 illustrates a block diagram of one embodiment of the controller 104. Generally, the controller 104 is comprised of one or more driver circuits 200 and receiver circuits 202. The driver circuits 200 are generally responsible for providing the stimulating signals over the lines 106 to the electrodes 108. That is, a processor 204, operating under software or hardware control, may instruct the driver circuit 200 to produce a stimulating signal having a set of preselected, desired parameters, such as frequency, duty cycle, duration, waveform shape, amplitude, voltage and magnitude. As noted above, driver circuits 200 may optionally include circuits 201 to generate pacing and/or high-voltage stimulation (denoted schematically in FIG. 2 as a part of driver circuit 200) to the heart on leads 109.

The receiver circuits 202 are generally responsible for receiving signals over the lines 112 from the sensors 110 and 111, and processing those signals into a form, such as a digital format, which may be analyzed by the processor 204 and/or stored in a memory 206, such as a dynamic random access memory (DRAM). The memory 206 may also store software, which is used to control the operation of the processor 204.

In one embodiment, signals stored in memory 206 may be transferred via a communication circuit 207 such as a telemetry circuit to an external device 209 such as a programmer. These signals may be stored in the external device, or transferred via a network 211 to a remote system 213 which may be a repository or some other remote database. Network 211 may be an intranet, internet system such as the world-wide web, or any other type of communication link.

As noted above, controller 104 may further include a drug delivery device 217 that may comprise a pump coupled to a catheter 215. Exemplary implantable drug delivery systems that may be adapted to deliver biologically-active agents in conjunction with SCS or other nerve stimulation are disclosed in U.S. Pat. No. 5,607,418, issued to Arzbaecher, U.S. Pat. No. 5,220,917, issued to Carnilli, U.S. Pat. No. 4,146,029, issued to Ellinwood and U.S. Pat. No. 5,330,505, issued to Cohen, all incorporated herein by reference in their entireties.

Figure 3:
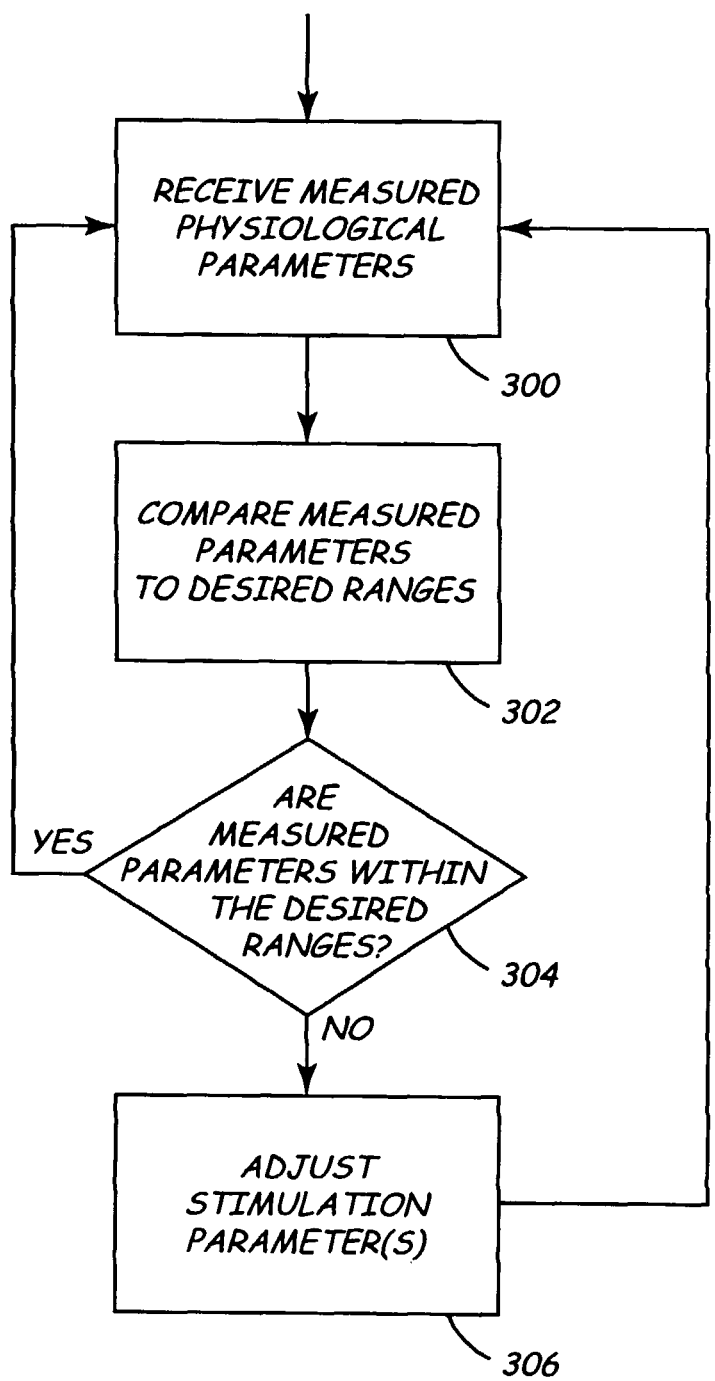
FIG. 3 illustrates a stylized flowchart of a control routine that may be performed by the controller of FIGS. 1 and 2.

The overall general operation of the controller 104 may be appreciated by reference to a flowchart depicted in FIG. 3. Those skilled in the art will appreciate that the flowchart illustrated herein may be used to represent either software that may be executed by the processor 204 or hardware configured to operate to perform the functions set forth in the flowchart. The process depicted in FIG. 3 begins at block 300 with the assumption that a cardiac event may have been detected either automatically or manually, but in any event, therapy is being administered by the controller 104.

At block 300, the processor 204 receives the measured physiological parameters via the receiver circuits 202. At block 302, the processor 204 compares the measured parameters to corresponding desired ranges. If the measure parameters are within the desired range, as determined at block 304, the processor 204 returns to block 300 and the process repeats. On the other hand, if the measured parameters fall outside the desired range, then the processor 204 at block 306 adjusts the stimulation parameter, which should result in the physiological parameters of the patient being adjusted to fall within the desired range. Thereafter, the process returns to block 300 and the process begins anew.

It should be appreciated that, owing to physiological differences between patients, an adjustment to the stimulation parameters may not produce an immediate, precise change in all patients. Rather, it is anticipated that each patient will respond substantially uniquely to variations in the stimulation parameters. Thus, it may be useful to add controllable variability to the operation of the feedback arrangement described herein. For example, it may be useful to control the rate at which the stimulation parameters are allowed to change, or to develop a histogram for a particular patient. The inventive system could include the ability to record parameters associated with the delivered SCS such as pulse widths, frequencies, duty cycles, and time varying patterns. These parameters and the patient's response may be recorded in the memory 206, for example. Based on patient response, the efficacy of the SCS can be evaluated so that the delivered SCS can be adjusted to further improve cardiac performance and efficiency. This "learning" capability allows the system to optimize SCS delivery based on prior patient data so that treatment is automatically tailored to individual patient needs. Furthermore, within a particular patient it may be useful for the device to tailor its therapy based on prior learning. For example, the onset or character of cardiac events may differ from episode to episode. It may be useful for the system to recognize multiple types of events (differing in, for example, severity, rate of onset, time of day or occurrence, patient activity levels, etc.) and treat these events with a uniquely tailored set of treatment parameters. Again, the device memory may be used to record parameters and patient responses to tailor treatments to different patterns of parameters.

In an alternative embodiment, a combined neuro and pacing stimulator Implantable Pulse Generator with outputs for neural stimulation (e.g. SCS, TENs, sub-cutaneous, peripheral, etc.) is provided. Lead attachments may be provided, in one instance, by a PISCES QUAD-type lead commercially-available from Medtronic Corporation, or an equivalent. Stimulation may be used in conjunction with cardiac resynchronization or other pacing therapy to improve cardiac function and may further be optimized based on some diagnostic parameter such as pressure, impedance, volume, or dimension, as discussed above. The Implantable Pulse Generator may further include a drug delivery system so that drug therapy to improve cardiac function may be automatically titrated with the stimulation. The implantable pulse generator may further includes a patient monitoring, diagnostic, or management system so that diagnostic and patient information therapy to improve cardiac function may be used in conjunction with neural stimulation.

In another embodiment, Spinal Cord Stimulation (SCS) may be performed at cervical levels C1-C8 instead of, or in addition to, T1-T12 stimulation. In yet another embodiment, Peripheral Nerve Stimulation (PNS) may be performed at C2, C3, median, peroneal, ulnar, ansa lenticularis, and/or dorsal root ganglia to improve cardiac performance and efficiency.

In all of the above-described embodiments, the electrical stimulation is described as SCS, which may be delivered using one or more implanted electrodes located adjacent the spine, for example. However, it will be understood that stimulation using externally-applied electrodes, or subcutaneous electrodes located under the skin may also be used to obtain the benefits discussed above. In the case of an externally-applied electrode system, a portable stimulation device carried or worn externally by the patient may be used to provide treatment.

In one embodiment, a paddle-type (flat) lead having a surface area between one square cm and five square inches or more may be used to accomplish the subcutaneous stimulation. Such a lead may be formed of an insulative material, with programmable electrodes on one or more of the flat sides of the lead for either skin stimulation, muscle stimulation, or both.

In one embodiment, electrodes may be provided on both sides of the lead, with the electrodes employed for stimulation at a given time being selectively enabled by a user. Alternatively, the system may be programmable to select the type of tissue to be stimulated. This is desirable since in some instances, it may be beneficial to provide stimulation to only spinal neurons, whereas in other instances it may be desirable to also stimulate skin nerves, muscle nerves, peripheral nerves, cranial nerves, such as the vagus, ganglia and plexi, or any combination of such nervous tissue. Various electrode combinations could be provided to allow for selectively enabling the stimulation in this manner.

In another embodiment, the paddle-type lead is between four and ten millimeters wide to easily pass through a twelve-gage needle before it unfolds. A special needle may be provided having an oval or rectangular cross-section of appropriate size to allow for the delivery of this type of lead. Electrodes may be provided on one or both sides of the paddle lead. In yet another embodiment, the electrodes of a cutaneous stimulation system could be placed on the chest wall, or a stimulation source may be attached to leads passed via needles to one or more subcutaneous sites. Alternatively, electrodes may be placed on an outside surface of an implanted pulse generator or pacing device or may be of the type integrally formed with the can, shell, or housing of an implantable device.

Figure 4:
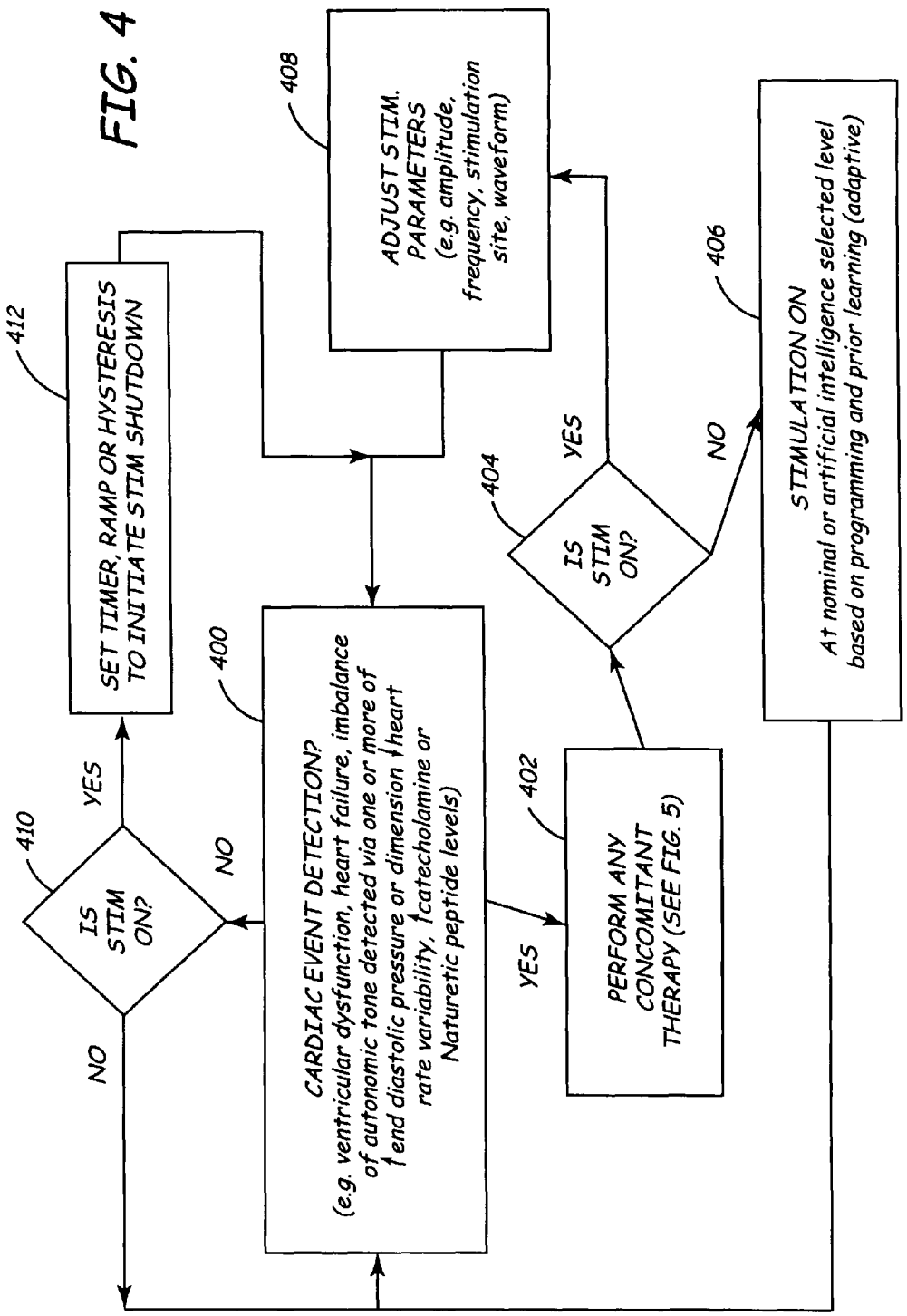
FIG. 4 is a flowchart illustrating one embodiment of the current invention.

FIG. 4 is a flowchart illustrating one embodiment of the current invention. A cardiac event such as ventricular dysfunction, heart failure, or imbalance of autonomic tone or neuro-endocrinological system may be detected using measurable parameters such as increased diastolic pressure, a lower heart rate variability, increased catecholiamine levels, or a change in naturetic peptide levels (400). If a cardiac event is detected, any concomitant therapies are performed (402). If neural stimulation is not on (404), it is activated (406). This therapy delivery may involve use of artificial intelligence or other learning capability, as discussed above. Monitoring continues to determine whether the cardiac condition still exists (400). Returning to step 404, if neural stimulation is already on, stimulation parameters may be adjusted using physiological signals that may be sensed by sensors 110 and 111 (408), and monitoring continues with step 400.

In block 400, if a cardiac event has terminated, processing continues to step 410, where it is determined whether stimulation is on. If not, processing continues with monitoring step 400. Otherwise, stimulation deactivation is initiated (412). This may involve a hysteresis so that stimulation is terminated gradually over a predetermined period of time.

Figure 5:
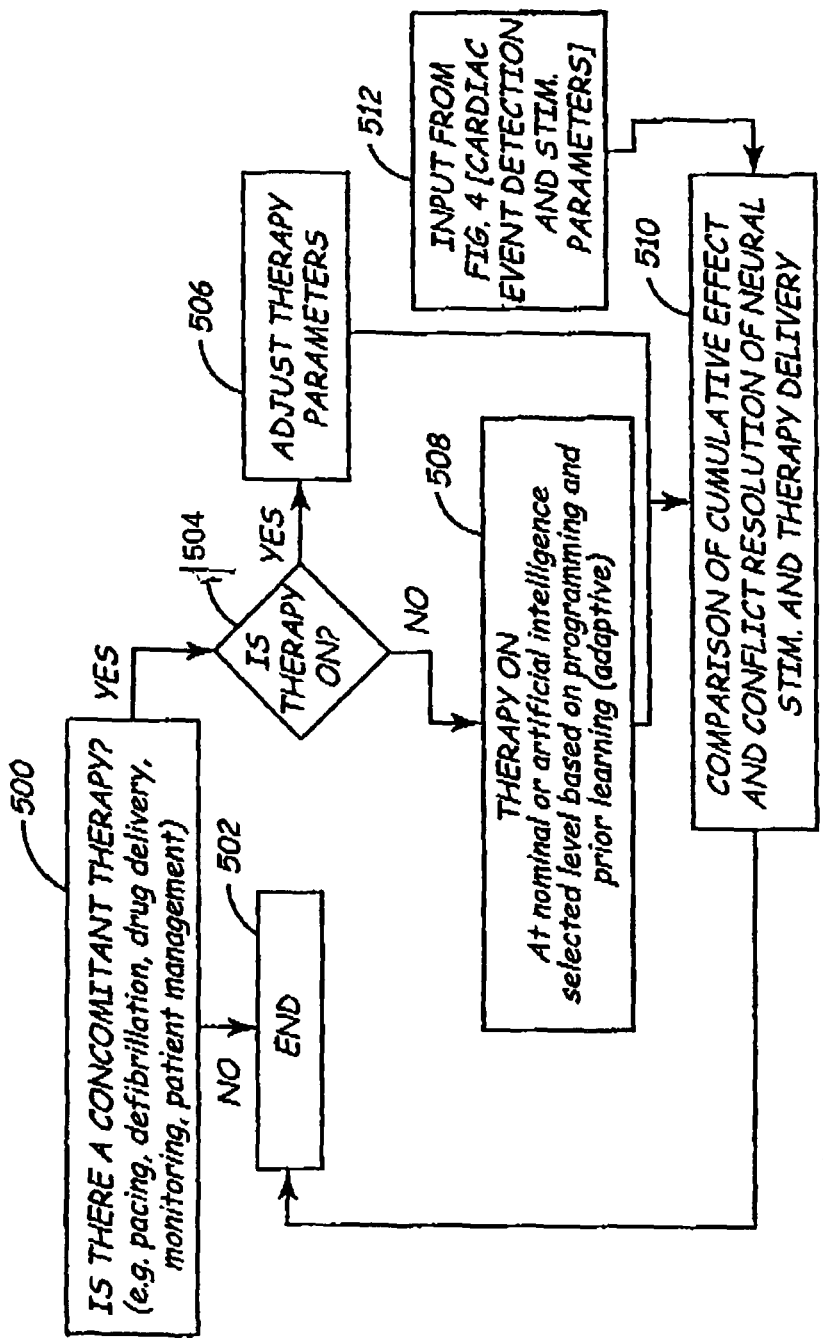
FIG. 5 is a flowchart illustrating one embodiment of concomitant therapy delivery that may be provided in conjunction with neural stimulation.

FIG. 5 is a flowchart illustrating one embodiment of concomitant therapy delivery that may be provided in conjunction with neural stimulation. This therapy corresponds to that shown in step 402 of FIG. 4. This type of therapy may involve pacing, defibrillation, drug delivery, monitoring, and/or patient management therapies, for example (500). If such a therapy is not enabled, no action is taken (502). Otherwise, if the therapy is on therapy parameters may be adjusted (506). This may be performed using sensed physiological parameters, for example. If therapy is not enabled, this therapy is activated (508). Therapy delivery may be based on the results of previously-delivered therapy in the manner discussed above, as may be accomplished using artificial intelligence capabilities, for example. In either event, processing continues by comparing the cumulative effects of neural stimulation and the other therapy delivery so that the therapy delivery may be adjusted, if necessary (510). For example, delivery of stimulation to nerve tissue could increase pacing thresholds associated with a concomitant pacing therapy. As a result, the pacing therapy may need to be adjusted. In another example, delivery of stimulation according to the current invention may reduce pulse pressure, whereas a bi-ventricular pacing regimen increases the pulse pressure. It may be desirable to monitor this interaction and adjust one or more therapies as needed. This step is performed using information provided by the sensors, the neural stimulation system, and the concomitant therapy system(s), as shown in block 512.

From the foregoing discussion, one skilled in the art will appreciate that the current system and method for treating ventricular dysfunction, heart failure, or imbalance of the autonomic tone allows the treatment to be titrated without regard to a patient's compliance. Additionally, more patients will be able to use the therapy because of general lack of side-effects.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. An apparatus for treating a patient to improve cardiac performance and efficiency of the patient's heart, the apparatus comprising:
at least one electrode adapted to be located in a region associated with nervous tissue in a patient;
means for monitoring one or more physiologic parameters of the patient;
means for automatically applying electrical stimulation via the at least one electrode to improve balance of a neuro-endocrinological system of the patient in response to the one or more physiologic parameters of the patient; and
means for delivering a pacing therapy to the patient's heart of a type that improves cardiac output, wherein said pacing therapy consists of a cardiac resynchronization therapy; and
means for adjusting the electrical stimulation applied during delivery of the pacing therapy responsive to the one or more physiological parameters of the patient as monitored during delivery of the pacing therapy.

2. The apparatus of claim 1, wherein the at least one electrode further comprises at least one implanted electrode adapted to be located adjacent a patient's spine.

3. The apparatus of claim 1, wherein the at least one electrode is adapted to be located external to and in direct contact with a portion of skin of the patient's.

4. The apparatus of claim 1, wherein the at least one electrode is adapted to be located in a subcutaneous space of the patient's body.

5. The apparatus of claim 1 wherein delivery of the pacing therapy comprises altering a previously delivered pacing therapy in conjunction with applying the electrical stimulation.

6. The apparatus of claim 1 wherein delivery of the pacing therapy comprises initiating delivery of the pacing therapy in conjunction with applying the electrical stimulation.

7. The apparatus of claim 1 wherein the monitoring means comprises a pressure sensor.

8. The apparatus of claim 1 wherein the monitoring means comprises a pressure sensor adapted for a cardiac location.

9. The apparatus of claim 8 wherein the monitoring means comprises means for determining the patient's diastolic pressure.

10. The apparatus of claim 1 wherein the monitoring means comprises means for sensing heart rate.

11. The apparatus of claim 10 wherein the monitoring means comprises means for sensing heart rate variability.

* * * * *